United States Patent
Vilsmeier et al.

(10) Patent No.: US 11,682,115 B2
(45) Date of Patent: Jun. 20, 2023

(54) ATLAS-BASED LOCATION DETERMINATION OF AN ANATOMICAL REGION OF INTEREST

(71) Applicant: Brainlab AG, Munich (DE)

(72) Inventors: Stefan Vilsmeier, Munich (DE); Clara Orlando, Bern (CH); Ron Zenvirt, Mevaseret Zion (IL)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 17/038,542

(22) PCT Filed: Aug. 4, 2019

(86) PCT No.: PCT/IL2019/050884
§ 371 (c)(1),
(2) Date: Sep. 30, 2020

(87) PCT Pub. No.: WO2021/024242
PCT Pub. Date: Feb. 11, 2021

(65) Prior Publication Data
US 2022/0215551 A1    Jul. 7, 2022

(51) Int. Cl.
*G06K 9/00*     (2022.01)
*G06T 7/00*     (2017.01)
(Continued)

(52) U.S. Cl.
CPC .......... *G06T 7/0014* (2013.01); *G06T 3/0006* (2013.01); *G06T 7/30* (2017.01);
(Continued)

(58) Field of Classification Search
CPC .............................. G06T 7/0012–0016; G06T 2207/10064–10136;
(Continued)

(56) References Cited

U.S. PATENT DOCUMENTS 6,430,430 B1   8/2002 Gosche
7,646,898 B1 * 1/2010 Nowinski ................. G06T 7/33
                                            382/128
(Continued)

FOREIGN PATENT DOCUMENTS

EP        2819093        12/2014
WO      2005023086        3/2005

OTHER PUBLICATIONS

Phellan et al., "Improving Atlas-Based Medical Image Segmentation with a Relazed Object Search" In: "Serious Games", Springer International Publishing, Cham 032682, dated Jan. 1, 2014. 12 Pages.

(Continued)

*Primary Examiner* — Atiba O Fitzpatrick
(74) *Attorney, Agent, or Firm* — Gray Ice Higdon

(57) ABSTRACT

Disclosed is a computer-implemented method of determining an assignment of an object acquire patient image data of interest recognizable in a digital medical patient image such as a tumour or other medical anomaly such as an implant to an anatomical region. The medical patient image is registered with atlas data, The assignment is then determined by calculating a score value defining an amount of volume intersection between the object of interest and a digital object defining a specific anatomic region, for example a bounding box around a specific organ, which is defined in the atlas data.

11 Claims, 3 Drawing Sheets

(51) Int. Cl.
*G06T 7/62* (2017.01)
*G06T 7/30* (2017.01)
*G06T 7/70* (2017.01)
*G16H 10/60* (2018.01)
*G16H 30/20* (2018.01)
*G06V 10/25* (2022.01)
*G06V 10/764* (2022.01)
*G06T 3/00* (2006.01)

(52) U.S. Cl.
CPC .............. *G06T 7/62* (2017.01); *G06T 7/70* (2017.01); *G06V 10/25* (2022.01); *G06V 10/764* (2022.01); *G16H 10/60* (2018.01); *G16H 30/20* (2018.01); *G06T 2200/04* (2013.01); *G06T 2207/10072* (2013.01); *G06T 2207/30016* (2013.01); *G06T 2207/30036* (2013.01); *G06T 2207/30096* (2013.01); *G06T 2207/30101* (2013.01); *G06V 2201/03* (2022.01)

(58) Field of Classification Search
CPC ... G06T 2207/30004–30104; G06T 7/10–194; G06T 2207/20021; G06T 2207/20112–20168; G06T 2207/20128; G06T 7/75; G06T 7/70; G06T 7/73; G06T 7/74; G06T 7/77; G06T 7/30; G06T 7/32; G06T 7/33; G06T 7/337; G06T 7/344; G06T 7/35; G06T 3/0068; G06T 3/0075; G06T 7/13; G06T 7/149; G06T 7/155; G06T 7/12; G06T 7/181; G06T 7/60; G06T 7/62; G06V 2201/03–034; G06V 10/25–273; G06V 20/49; G06V 20/695; G06V 40/162; G06V 20/80; G06V 20/698; A61B 5/7485; G06K 9/6224
See application file for complete search history.

(56) References Cited

U.S. PATENT DOCUMENTS

| | | | |
|---|---|---|---|
| 2008/0080770 A1 | 4/2008 | Mendonca et al. | |
| 2010/0128946 A1* | 5/2010 | Fidrich | G06T 7/11 382/131 |
| 2012/0177263 A1* | 7/2012 | Akinyemi | G06T 7/11 382/128 |
| 2018/0096478 A1* | 4/2018 | Zhang | G16H 50/30 |
| 2021/0090265 A1* | 3/2021 | Han | G06N 3/08 |

OTHER PUBLICATIONS

Sharma et al., "Automated medical image segmentation techniques", Journal of Medical Physics, vol. 35, No. 1, 2010. 3 Pages.
International Search Report and Written Opinion issued in Application No. PCT/IL2019/050884 dated Sep. 18, 2019.

* cited by examiner

ATLAS-BASED LOCATION DETERMINATION OF AN ANATOMICAL REGION OF INTEREST

FIELD OF THE INVENTION

The present invention relates to a computer-implemented method of determining an assignment between a region of interest in a medical image of an anatomical body part to a virtual object defined in an image-based model, a corresponding computer program, a program storage medium storing such a program and a computer for executing the program, as well as a medical system comprising an electronic data storage device and the aforementioned computer.

TECHNICAL BACKGROUND

In a clinical research and analysis most patient information is stored in unstructured forms (e.g. medical notes) or in different labelling locations inside an electronic health record of a hospital. Clinical research today still relies on manual collection and manual enrichment of patient data which is very time consuming, in particular for large pool of patients.

Medical imaging data (DICOM) lacks metadata regarding the anatomical labelling location of objects of interest (e.g. tumors). This limits the number of information that can be used for further analysis and manual enrichment for clinical research is very time consuming for a large patient pool. Existing tools/methods providing labelling location detection features are limited to spherical tumors (i.e. brain metastases), or focus on specific diseases (e.g. multiple sclerosis).

The present invention has the object of providing an improved method of determining the location of a tumour relative to the patient's anatomy.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses determining an assignment of an object of interest recognizable in a digital medical patient image such as a tumour or other medical anomaly such as an implant to an anatomical region. The medical patient image is registered with atlas data, The assignment is then determined by calculating a score value defining an amount of volume intersection between the object of interest and a digital object defining a specific anatomic region, for example a bounding box around a specific organ, which is defined in the atlas data.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of determining an assignment between a region of interest in a medical image of an anatomical body part to a virtual object defined in an image-based model. The method comprises executing, on at least one processor of at least one computer (for example at least one computer being part of a navigation system), the following exemplary steps which are executed by the at least one processor.

In a (for example first) exemplary step, patient image data is acquired which describes a medical patient image of the anatomical body part including information about the position of an image representation in the medical patient image of a region of interest.

For example, the region of interest comprises or consists of an image representation of a medical anomaly being for example at least one of a tumour, a neural fibre, an implant, a cavity, a haemorrhage, a necrosis, an arteriovenous malformation or an electrode.

In a (for example second) exemplary step, atlas data is acquired which describes an image-based model of the anatomical body part which comprises virtual objects, each virtual object describing a subset of the anatomical body part. For example, wherein the atlas data describes an identifier (such as a label embodied for example by information in character electronic data format, for example by a string) for the at least one of the virtual objects described by the object assignment data, and wherein the method comprises a step of assigning the identifier to the region of interest. For example, the patient image data and the atlas data are defined in three dimensions and for example have been generated by applying a tomographic imaging modality such as computed x-ray tomography or magnetic resonance tomography or ultrasound tomography.

In a (for example third) exemplary step, atlas region registration data is determined based on the patient image data and the atlas data, wherein the atlas region registration data describes a mapping between the virtual objects defined in the image-based model and image constituents of the medical patient image, wherein the image constituents include the region of interest. The mapping is established for example by applying an image fusion algorithm to the patient image data and the atlas data.

In a (for example fourth) exemplary step, region ratio data is determined based on the atlas registration data and the patient image data, wherein the region ratio data describes a ratio between the volume of the region of interest and the volume of an intersection of the region of interest with each one of the virtual objects onto which an image constituent including the region of interest is mapped by the mapping between the virtual objects defined in the image-based model and constituents of the medical patient image.

In a (for example fifth) exemplary step, envelope data is determined based on the patient image data, wherein the envelope data describes the position of an envelope of the region of interest determined by deducting the region of interest from a dilation of the region of interest. The envelope is for example embodied by a bounding box around each virtual object. The envelope is a way of representing the surface of an image constituent defining e.g. a tumour and calculate how much of it touches a certain virtual object. In one example, the dilation of the region of interest is generated by applying an affine matrix deformation to the image representation of the region of interest in the patient image data. For example, an envelope is determined for each of the virtual objects which is defined by the extreme values of the coordinates of the position of the respective virtual object and wherein an envelope is determined for the region of interest which is defined by the extreme values of the coordinates of the position of the region of interest, and wherein a virtual object, the envelope of which does not intersect the envelope of the region of interest, is not considered (i.e. excluded from further analysis) for determining the object assignment data.

In a (for example sixth) exemplary step, atlas envelope registration data is determined based on the envelope data and the atlas data, wherein the atlas region registration data describes a mapping between the virtual objects defined in the image-based model and the envelope.

In a (for example seventh) exemplary step, envelope ratio data is determined based on the region envelope data and the atlas registration data, wherein the envelope ratio data describes a ratio between the volume of the envelope and the volume of an intersection of the envelope with each one of the virtual objects onto the surface of which the outer surface of the envelope is mapped by the mapping between the virtual objects defined in the image-based model and the envelope.

In a (for example eighth) exemplary step, score data is determined based on the region ratio data and the envelope ratio data, wherein the score data describes a score value being the greater of the ratio described by the region ratio data and the ratio described by the envelope ratio data. In one example, the score value is multiplied by a predetermined value which depends on the geometry of the region of interest and/or the geometry of the intersecting virtual object.

In a (for example ninth) exemplary step, object assignment data is determined based on the score data, wherein the object assignment data describes at least one of the virtual objects (for example, only the surface of at least one of the virtual objects or its envelope or the whole virtual object or envelope) onto which the region of interest or the envelope is mapped and for which the score value exceeds a predetermined threshold value. For example, the object assignment data is assigned to a location in the medical patient image which is not mapped (for example, because it lies in a space between organs) by the mapping defined by the atlas region registration data to any one of the virtual objects.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital, for example electronic, signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
a) the at least one computer according to the fourth aspect; and
b) at least one electronic data storage device storing at least the patient image data and the atlas data,
wherein the at least one computer is operably coupled to
the at least one electronic data storage device for acquiring, from the at least one data storage device, at least the patient image data and the atlas data, and
the at least one electronic data storage device for storing, in the at least one data storage device, the object assignment data.

In a sixth aspect, the invention is directed to a radiation treatment planning station comprising the system according to fifth aspect.

In a seventh aspect, the invention is directed to use of the method according to the first aspect for planning a radiation treatment procedure, wherein the use comprises execution of the steps of the method according to the first aspect.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of applying radiation such as ionizing radiation to the human or animal body for example to generate the patient image data or the atlas data or insert an object such as an electrode into the human or animal body. More particularly, the invention does not involve or in particular comprise or encompass any surgical or therapeutic activity. The invention is instead directed as applicable to acquiring, for example receiving and/or reading, the already generated patient image data and the atlas data as input to the method according to the first aspect. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) as mentioned by Wikipedia at https://en.wikipedia.org/wiki/Single-photon_emission_computed_tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
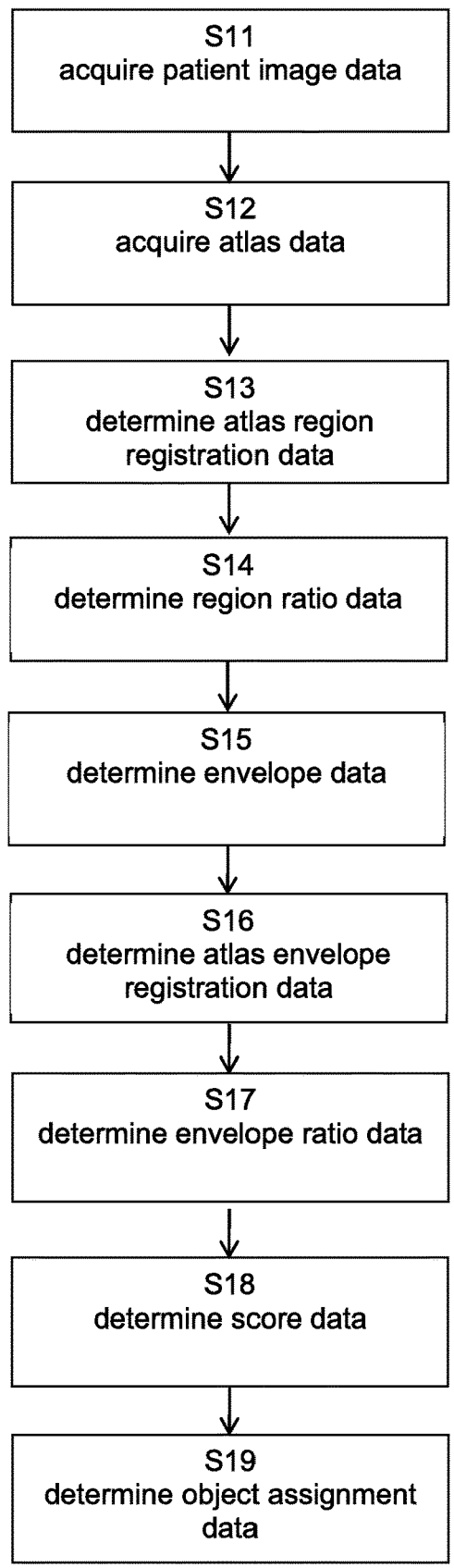
FIG. 1 illustrates the basic flow of the method according to the first aspect.
Figure 2:
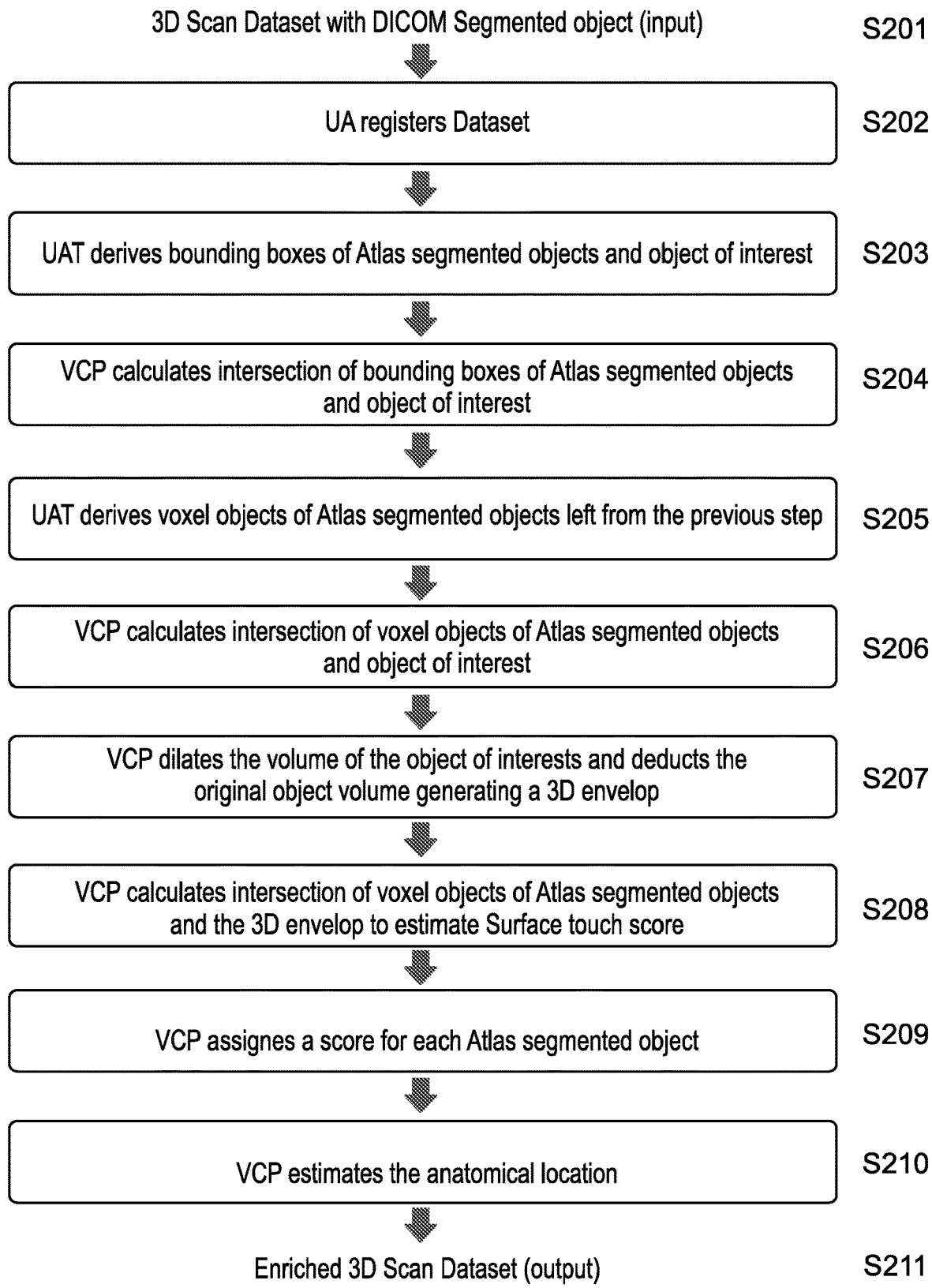
FIG. 2 shows an embodiment of the method according to the first aspect.

FIG. 1 illustrates the basic steps of the method according to the first aspect, in which step S11 encompasses acquisition of the patient image data and step S12 encompasses acquisition of the atlas data. On the basis of these data sets, subsequent step S13 determines the atlas region registration data, which in turn serves as a basis for determining the region ratio data in step S14. The method then continues with step S15 in which the envelope data is determined. The atlas envelope registration data is then determined in step S16, which is followed by step S17 encompassing determination of the envelope ratio data. Then, the score data is determined in step S18 which serves as an inout to step S19 in which the object assignment data is determined, FIG. 2 is a flow chart showing an example implementation of the method according to the first aspect in which the labelling location is estimated.

In step S201, the patient image data embodied by a three-dimensional scan data set is input. Then, the method in step S202 reads the atlas data embodied by a universal atlas (UA) and registers the medical patient image containing the object of interest into the universal atlas space. The following step S203 queries the universal atlas transfer (UAT) for the bounding boxes of pre-defined auto-segmented objects. Step S204 then calculates the intersection between the bounding box of each atlas-segmented object and the bounding box of the object of interest using a software module called "Volume Correlation Performer" (VCP). At this stage, any atlas-segmented object for which the intersection calculated in this stage is zero is filtered out. Step S205 encompasses querying the universal atlas for the actual atlas-segmented objects left after the latest preceding step (and not only their bounding-boxes as retrieved in step S203). In step S206, the method calculates the intersection of each atlas-segmented object (B) left after previous step with the volume of the object of interest (A). The resulting value (A ∩ B) represents the volume that contains all voxels of A that also belong to B. The value |A∩B|/|A| indicates the percentage of the object of interest which is located inside the atlas-segmented object. In subsequent step S207, the method enlarges (dilates) the volume of the object of interest by 0.2 mm to 0.8 mm (can be adjusted by future analysis) and deducts the original object volume generating a three-dimensional envelop. It is then calculated in subsequent step S208 the intersection of each atlas-segmented object (C) left with the three-dimensional envelope (D). The resulting value (C∩D) represents the part of the surrounding of the object of interest that touches the Atlas segmented object. The value |∩D|/|D| indicates the percentage of the surface of the object of interest which touches the Atlas segmented object. For each atlas-segmented object, the method in step S209 assigns the highest of the two values calculated in previous steps as the score of that location. Some anatomical locations may not be defined by intersection or inclusion but by the atlas-segmented object. The location with the highest score is considered in step S210 to be the estimated location of the object of interest. The method automatically matches overlapping/counterpart objects of interest (i.e. DICOM SEG objects) segmented by users on the same three-dimensional scan image or on longitudinal three-dimensional scan images and estimates their anatomical labelling location.

The anatomical labelling location of an object is estimated in e.g. six steps:

Step 1: Registration in Atlas Space

The method registers the medical patient image containing the object of interest with the atlas space (i.e. the atlas pre-defined objects (organs) are mapped into the patient image coordinate space).

Step 2: Inclusion-Exclusion Criteria

The Universal Atlas Transfer is queried for the bounding boxes (the maximum and minimum values of the x-y-z coordinates of each voxel in the object) of pre-defined auto-segmented objects. The method calculates the intersection between the bounding box of each atlas-segmented object and the bounding box of the object of interest. Atlas-segmented objects of disjoint pairs are excluded from subsequent steps. The universal atlas registration for the atlas-segmented objects left after the last step is refined, and the refined objects are then received.

Step 3: Volume Intersection Calculation

The method calculates the intersection of each Atlas segmented object (B) left after step 2 with the volume of the object of interest (A). The resulting value (A ∩B) represents the volume that contains all voxels of A that also belong to B. The value |A∩B|/|A| indicates the percentage of the object of interest which is located inside the Atlas segmented object.

Step 4: Surface Touch Amount Calculation

The method enlarges (dilates) the volume of the object of interest by 0.2 mm to 0.8 mm (can be adjusted by future analysis) and deducts the original object volume generating a three-dimensional envelop. It then calculates the intersection of each atlas-segmented object (C) left after step 2 with the 3D envelop (D). The resulting value (C ∩D) represents the part of the surrounding of the object of interest that touches the atlas-segmented object. The value |C∩D|/|D| indicates the percentage of the surface of the object of interest which touches the atlas-segmented object.

Step 5: Score Calculation

For each atlas-segmented object the tool assigns the highest of the two values calculated in step 3 and 4 as the score of that location.

Some anatomical location are not organs detectable by the atlas, but can be defined by the organs (atlas-segmented objects) which they touch (e.g. the cerebellopontine angle (CPA) is located between cerebellum and brainstem). In those cases, the score assigned to the location is calculated as the sum of the scores of the surrounding locations multiplied by a factor between 0.5 and 1, including those boundary values. For instance, the score of the CPA is calculated according to the following formula:

$$CPA=(C+BS)*f \text{ (for example, } f=0.9)$$

where CPA is the cerebellopontine angle, C is the calculated score for the cerebellum, and BS is the calculated score for brainstem. If the volume of the object of interest touches both structures (C and BS) the resulting score will be higher as long as the score of the cerebellum and brainstem are similar.

Some anatomical locations might require the addition of a factor to the score due to the unusual shape. For instance, the optic nerve is a very thin and long structure and a tumor object in this location might be larger resulting in a low score. The score of such locations is multiplied by an extra factor defined per location.

Step 6: Location Estimation

The location with the highest score as defined in step 5 is considered the estimated location of the object of interest.

Figure 3:
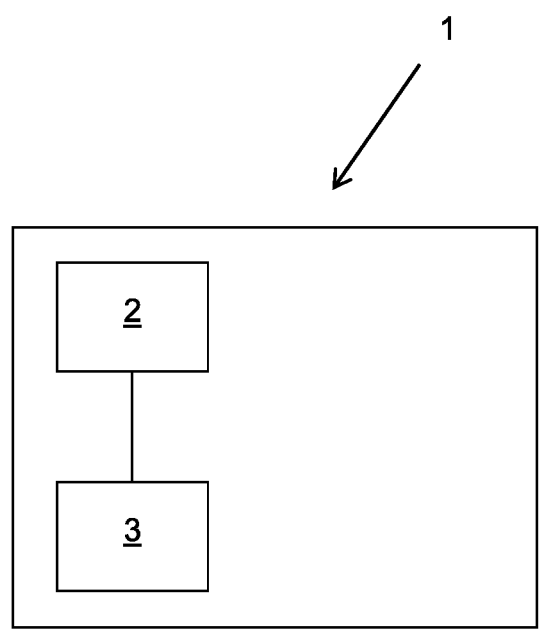
FIG. 3 is a schematic illustration of the system according to the fifth aspect.

FIG. 3 is a schematic illustration of the medical system 1 according to the fifth aspect. The system is in its entirety identified by reference sign 1 and comprises a computer 2, at least one electronic data storage device (such as a hard disc) 3 for storing at least the patient image data and the atlas data. The components of the medical system 1 have the functionalities and properties explained above with regard to the fifth aspect of this disclosure.

The method according to the first aspect may be embodied by a software module called Anatomical Label Performer (ALP) which is a general-purpose, extensible, DICOM image processing tool that automatically estimates the anatomical labelling location of an object of interest segmented on a three-dimensional scan image. This new feature is referred in this disclosure as "labelling location estimation".

Imaging and image analysis have become an essential component in many fields of medical research and clinical practice. Thus, possible applications of such tool include (but are not limited to):

clinical research (e.g. cancer registry) with automatic data enrichment 13 the method enriches and adds value to the sets of image data routinely obtained in the clinical setting and used for research; and tumour board meetings, where unambiguous evaluation of tumour progression over time is crucial for management of tumour patients.

In addition, any priority document(s) of this application is/are hereby incorporated herein by reference in its/their entirety.

The invention claimed is:

1. A computer-implemented medical method of determining an assignment between a region of interest in a medical image of an anatomical body part to a virtual object defined in an image-based model, the method comprising the following steps:

patient image data is acquired which describes a medical patient image of the anatomical body part including information about the position of an image representation in the medical patient image of a region of interest;

atlas data is acquired which describes an image-based model of the anatomical body part which comprises virtual objects, each virtual object describing a subset of the anatomical body part;

atlas region registration data is determined based on the patient image data and the atlas data, wherein the atlas region registration data describes a mapping between the virtual objects defined in the image-based model and image constituents of the medical patient image, wherein the image constituents include the region of interest;

region ratio data is determined based on the atlas region registration data and the patient image data, wherein the region ratio data describes a ratio between the volume of the region of interest and the volume of an intersection of the region of interest with each one of the virtual objects onto which an image constituent including the region of interest is mapped by the mapping between the virtual objects defined in the image-based model and constituents of the medical patient image;

envelope data is determined based on the patient image data, wherein the envelope data describes the position of an envelope of the region of interest determined by deducting the region of interest from a dilation of the region of interest;

atlas envelope registration data is determined based on the envelope data and the atlas data, wherein the atlas envelope registration data describes a mapping between the virtual objects defined in the image-based model and the envelope;

envelope ratio data is determined based on the envelope data and the atlas region registration data, wherein the envelope ratio data describes a ratio between the volume of the envelope and the volume of an intersection of the envelope with each one of the virtual objects onto the surface of which respective virtual object the outer surface of the envelope is mapped by the mapping between the virtual objects defined in the image-based model and the envelope;

score data is determined based on the region ratio data and the envelope ratio data, wherein the score data describes a score value being the greater of the ratio described by the region ratio data and the ratio described by the envelope ratio data;

object assignment data is determined based on the score data, wherein the object assignment data describes at least one of the virtual objects onto which the region of interest or the envelope is mapped and for which the score value exceeds a predetermined threshold value.

2. The method according to claim 1, wherein the region of interest comprises or consists of an image representation of a medical anomaly at least one of a tumour, a neural fibre, an implant, a cavity, a haemorrhage, a necrosis, an arteriovenous malformation or an electrode.

3. The method according to claim 1, wherein an envelope is determined for each of the virtual objects which is defined by the extreme values of the coordinates of the position of the respective virtual object and wherein an envelope is determined for the region of interest which is defined by the extreme values of the coordinates of the position of the region of interest, and wherein a virtual object, the envelope of which does not intersect the envelope of the region of interest, is not considered for determining the object assignment data.

4. The method according to claim 1, wherein the score value is multiplied by a predetermined value which depends on the geometry of the region of interest.

5. The method according to claim 1, wherein the dilation of the region of interest is generated by applying an affine matrix deformation to the image representation of the region of interest in the patient image data.

6. The method according to claim 1, wherein the object assignment data is assigned to a location in the medical patient image which is not mapped by the mapping defined by the atlas region registration data to any one of the virtual objects.

7. The method according to claim 1, wherein the atlas data describes an identifier for the at least one of the virtual objects described by the object assignment data, and wherein the method comprises a step of assigning the identifier to the region of interest.

8. The method according to claim 1, wherein the patient image data and the atlas data are defined in three dimensions and have been generated by applying a tomographic imaging modality.

9. A non-transitory computer readable storage media comprising instructions executable by at least one processor that when executed cause the at least one processor to:

acquire patient image data which describes a medical patient image of the anatomical body part including information about the position of an image representation in the medical patient image of a region of interest;

acquire atlas data which describes an image-based model of the anatomical body part which comprises virtual objects, each virtual object describing a subset of the anatomical body part;

determine atlas region registration data based on the patient image data and the atlas data, wherein the atlas region registration data describes a mapping between the virtual objects defined in the image-based model and image constituents of the medical patient image, wherein the image constituents include the region of interest;

determine region ratio data based on the atlas region registration data and the patient image data, wherein the region ratio data describes a ratio between the volume of the region of interest and the volume of an intersection of the region of interest with each one of the virtual objects onto which an image constituent including the region of interest is mapped by the mapping between the virtual objects defined in the image-based model and constituents of the medical patient image;

determine envelope data based on the patient image data, wherein the envelope data describes the position of an envelope of the region of interest determined by deducting the region of interest from a dilation of the region of interest;

determine atlas envelope registration data based on the envelope data and the atlas data, wherein the atlas envelope registration data describes a mapping between the virtual objects defined in the image-based model and the envelope;

determine envelope ratio data based on the envelope data and the atlas region registration data, wherein the envelope ratio data describes a ratio between the volume of the envelope and the volume of an intersection of the envelope with each one of the virtual objects onto the surface of which respective virtual object the outer surface of the envelope is mapped by the mapping between the virtual objects defined in the image-based model and the envelope;

determine score data is based on the region ratio data and the envelope ratio data, wherein the score data describes a score value being the greater of the ratio described by the region ratio data and the ratio described by the envelope ratio data;

determine object assignment data based on the score data, wherein the object assignment data describes at least one of the virtual objects onto which the region of interest or the envelope is mapped and for which the score value exceeds a predetermined threshold value.

10. A computer comprising at least one processor and a memory, wherein the the memory having instructions that when executed, cause the at least one processor to:
- acquire patient image data which describes a medical patient image of the anatomical body part including information about the position of an image representation in the medical patient image of a region of interest;
- acquire atlas data which describes an image-based model of the anatomical body part which comprises virtual objects, each virtual object describing a subset of the anatomical body part;
- determine atlas region registration data based on the patient image data and the atlas data, wherein the atlas region registration data describes a mapping between the virtual objects defined in the image-based model and image constituents of the medical patient image, wherein the image constituents include the region of interest;
- determine region ratio data based on the atlas region registration data and the patient image data, wherein the region ratio data describes a ratio between the volume of the region of interest and the volume of an intersection of the region of interest with each one of the virtual objects onto which an image constituent including the region of interest is mapped by the mapping between the virtual objects defined in the image-based model and constituents of the medical patient image;
- determine envelope data based on the patient image data, wherein the envelope data describes the position of an envelope of the region of interest determined by deducting the region of interest from a dilation of the region of interest;
- determine atlas envelope registration data based on the envelope data and the atlas data, wherein the atlas envelope registration data describes a mapping between the virtual objects defined in the image-based model and the envelope;
- determine envelope ratio data based on the envelope data and the atlas region registration data, wherein the envelope ratio data describes a ratio between the volume of the envelope and the volume of an intersection of the envelope with each one of the virtual objects onto the surface of which respective virtual object the outer surface of the envelope is mapped by the mapping between the virtual objects defined in the image-based model and the envelope;
- determine score data is based on the region ratio data and the envelope ratio data, wherein the score data describes a score value being the greater of the ratio described by the region ratio data and the ratio described by the envelope ratio data;
- determine object assignment data based on the score data, wherein the object assignment data describes at least one of the virtual objects onto which the region of interest or the envelope is mapped and for which the score value exceeds a predetermined threshold value.

11. A medical system, comprising:
- at least one computer having at least one processor and memory having instructions that when executed, cause the at least one processor to:
  - acquire patient image data which describes a medical patient image of the anatomical body part including information about the position of an image representation in the medical patient image of a region of interest;
  - acquire atlas data which describes an image-based model of the anatomical body part which comprises virtual objects, each virtual object describing a subset of the anatomical body part;
  - determine atlas region registration data based on the patient image data and the atlas data, wherein the atlas region registration data describes a mapping between the virtual objects defined in the image-based model and image constituents of the medical patient image, wherein the image constituents include the region of interest;
  - determine region ratio data based on the atlas region registration data and the patient image data, wherein the region ratio data describes a ratio between the volume of the region of interest and the volume of an intersection of the region of interest with each one of the virtual objects onto which an image constituent including the region of interest is mapped by the mapping between the virtual objects defined in the image-based model and constituents of the medical patient image;
  - determine envelope data based on the patient image data, wherein the envelope data describes the position of an envelope of the region of interest determined by deducting the region of interest from a dilation of the region of interest;
  - determine atlas envelope registration data based on the envelope data and the atlas data, wherein the atlas region registration data describes a mapping between the virtual objects defined in the image-based model and the envelope;
  - determine envelope ratio data based on the region envelope data and the atlas region registration data, wherein the envelope ratio data describes a ratio between the volume of the envelope and the volume of an intersection of the envelope with each one of the virtual objects onto the surface of which respective virtual object the outer surface of the envelope is mapped by the mapping between the virtual objects defined in the image-based model and the envelope;
  - determine score data is based on the region ratio data and the envelope ratio data, wherein the score data describes a score value being the greater of the ratio described by the region ratio data and the ratio described by the envelope ratio data;
  - determine object assignment data based on the score data, wherein the object assignment data describes at least one of the virtual objects onto which the region of interest or the envelope is mapped and for which the score value exceeds a predetermined threshold value;
- at least one electronic data storage device storing at least the patient image data and the atlas data;
- wherein the at least one computer is operably coupled to
  - the at least one electronic data storage device for acquiring, from the at least one data storage device, at least the patient image data and the atlas data, and
  - the at least one electronic data storage device for storing, in the at least one data storage device, the object assignment data.

* * * * *

UNITED STATES PATENT AND TRADEMARK OFFICE
CERTIFICATE OF CORRECTION

PATENT NO. : 11,682,115 B2
APPLICATION NO. : 17/038542
DATED : June 20, 2023
INVENTOR(S) : Stefan Vilsmeier, Clara Orlando and Ron Zenvirt It is certified that error appears in the above-identified patent and that said Letters Patent is hereby corrected as shown below:

In the Specification

In Column 13, Line 3, delete "|∩D|/|D|" and insert -- ||C∩D| / |D| --, therefor.

In the Claims

In Column 17, Claim 10, Line 2, delete "the the" and insert -- the --, therefor.

In Column 17, Claim 11, Line 60, after "a" delete -- medical --.

Signed and Sealed this
Third Day of October, 2023

Katherine Kelly Vidal
*Director of the United States Patent and Trademark Office*